United States Patent [19]

Gundersen et al.

[11] Patent Number: 5,346,690
[45] Date of Patent: Sep. 13, 1994

[54] COMPOSITION OF A SUPERPARAMAGNETIC OR FERROMAGNETIC PARTICLE AND AN X-RAY CONTRAST AGENT FOR MRI

[75] Inventors: Helge G. Gundersen; Jo Klaveness, both of Oslo, Norway

[73] Assignee: Nycomed Imaging AS, Oslo, Norway

[21] Appl. No.: 820,643

[22] PCT Filed: Jul. 19, 1990

[86] PCT No.: PCT/EP90/01195
§ 371 Date: Jan. 21, 1992
§ 102(e) Date: Jan. 21, 1992

[87] PCT Pub. No.: WO91/01147
PCT Pub. Date: Feb. 7, 1991

[30] Foreign Application Priority Data

Jul. 21, 1989 [GB] United Kingdom ............ 8916782.9

[51] Int. Cl.$^5$ .................... A61B 5/055; A61K 31/195
[52] U.S. Cl. ........................................ 424/9; 424/646; 424/648; 424/5; 436/173; 128/653.4; 128/654; 514/492; 514/502; 514/563; 514/937; 562/473
[58] Field of Search ............. 424/9, 646, 648, 5; 514/937, 563, 492, 502; 436/173; 128/653.4, 654; 562/473

[56] References Cited

U.S. PATENT DOCUMENTS

| | | | |
|---|---|---|---|
| 4,698,302 | 10/1987 | Whitehead et al. | 435/94 |
| 5,114,703 | 5/1992 | Wolf et al. | 424/5 |
| 5,141,739 | 8/1992 | Jung et al. | 424/4 |
| 5,160,725 | 11/1992 | Pilgrimm et al. | 424/9 |
| 5,242,683 | 9/1993 | Klaveness | 424/9 |

FOREIGN PATENT DOCUMENTS

| | | |
|---|---|---|
| 0124766 | 11/1984 | European Pat. Off. |
| 0186947 | 7/1986 | European Pat. Off. |
| 0284549 | 9/1988 | European Pat. Off. |
| WO85/04530 | 10/1985 | PCT Int'l Appl. |

OTHER PUBLICATIONS

Aime, *Chemical Abstracts*, 110:91376f, 1989.
Lantos, *Biochemical Abstracts*, 87:132006, 1989.
Lauterbur et al., "Electrons to Tissues–Frontiers of Biological Energetics," vol. 1, Academic Press, New York, 1978.
Wesbey et al., *Radiology*, 149, 175–180, 1983.
Runge et al., *Radiology*, 147, 789–791, 1983.
Laniado et al., *Fortschr. Rontgenstr.*, 147, 325–332, 1987.
Kornmesser et al., *Fortschr. Rontgenstr.*, 147, 550–556, 1987.
Claussen et al., *Fortschr. Rontgenstr.*, 148, 683–689, 1987.
Lonnemark et al., *Acta Radiologica*, 29, 599, 1988.
Lonnemark et al., *Acta Radiologica*, 30, 193–196, 1989.
Mattrey et al., *AJR*, 148, 1259, 1987.
Wesbey et al., *Magn. Reson. Imag.*, 3, 57–64, 1985.
Hemmingsson et al., *Acta Radiologica*, 30, 29–33, 1989.
Society of Magnetic Resonance in Medicine, Book of Abstracts, vol. 1, 1990, p. 155. Ballinger, R. et al.
Kirk Othmer "Concise Encyclopedia of Chemical Technology," p. 55, John Wiley & Sons, New York (1989).

*Primary Examiner*—Gary E. Hollinden
*Attorney, Agent, or Firm*—Bacon & Thomas

[57] ABSTRACT

There is provided a magnetic resonance contrast medium comprising magnetically responsive particles and a physiologically tolerable osmoactive agent.

19 Claims, No Drawings

COMPOSITION OF A SUPERPARAMAGNETIC OR FERROMAGNETIC PARTICLE AND AN X-RAY CONTRAST AGENT FOR MRI

The present invention relates to improvements in and relating to magnetic resonance imaging (MRI), and in particular to contrast media for use in MRI, especially of body cavities from which contrast media may be discharged from the body without passing through body tissue, in particular the gastrointestinal (GI) system.

MRI is now a well established medical diagnostic tool which is particularly attractive to physicians, at least in part due to its ability to differentiate between soft tissues and since it does not require the patient to be exposed to the potentially harmful ionizing radiation, e.g. X-radiation and gamma-radiation, of conventional radiography.

Although MRI can be carried out without using added contrast media, it has found that image contrast can be improved by administering to the patient substances which affect the nuclear spin reequilibration of the nuclei (hereinafter the "imaging nuclei"—generally water protons in body fluids and tissues) that are responsible for the magnetic resonance (MR) signals from which MR images are generated.

Accordingly, in recent years, many such substances have been suggested for use as MRI contrast agents. Thus, for example, in 1978 Lauterbur proposed the use of paramagnetic species, such as Mn(II), as MRI contrast agents (see Lauterbur et al., pages 752–759 in "Electrons to Tissues—Frontiers of Biological Energetics", Volume 1, edited by Dutton et al., Academic Press, New York, 1978). More recently Schering AG, in EP-A-71564, proposed the use of the dimeglumine salt of the gadolinium(III) chelate of diethylenetriaminepentaacetic acid (GdDTPA-dimeglumine).

While MRI has until now mainly been used for imaging the central nervous system, the technique has great potential for imaging externally voided body cavities and especially the GI tract. However, development of MRI as a technique for imaging the GI tract, or indeed the abdomen in general, has been hindered by the special problems of imaging the abdomen in which, in the absence of a contrast agent, inter-tissue contrast is relatively poor. There is thus a general need for improved MRI contrast media suitable for imaging such body cavities.

Various substances have been evaluated as potential MRI contrast agents for the GI system, including for example paramagnetic compounds, perfluorochemicals and magnetically responsive particles (that is ferromagnetic, ferrimagnetic or superparamagnetic particles). In this regard, reference may be had to Wesbey et al. Radiology 149: 175–180 (1983), Runge et al. Radiology 147: 789–791 (1983), Laniado et al. Fortschr. Röntgenstr. 147: 325–332 (1987), Kornmesser et al. Fortschr. Röntgenstr. 147: 550–556 (1987), Claussen et al. Fortschr. Röntgenstr. 148: 683–689 (1988), Lönnemark et al. Acta Radiologica 29: 599 (1988), Lönnemark et al. Acta Radiologica 30: 193–196 (1989) Fasc. 2, Mattrey et al. AJR 148: 1259 (1987), and Wesbey et al. Magn. Reson. Imag. 3: 57–64 (1985) and to references therein.

Two products at least are now in clinical trials as oral MRI contrast media—suspensions of magnetically responsive particles (see Lönnemark et al. (1989) supra) and solutions of GdDTPA-dimeglumine (see Claussen et al. supra).

From a diagnostic point of view, magnetically responsive particles and paramagnetic metal chelates such as GdDTPA produce completely different contrast enhancements in MR images. Thus GdDTPA is a "positive" contrast agent, i.e. its effect of reducing the spin-lattice relaxation time ($T_1$) of the imaging nuclei results in an iincrease in the image intensity for the body regions into which it distributes. Magnetically responsive particles on the other hand are "negative" contrast agents, so called since their effect of reducing the spin-spin relaxation time ($T_2$) of the imaging nuclei outweighs the effect of $T_1$ reduction and results in a decrease in the MR signal intensity from the body regions into which they distribute.

The two forms of contrast enhancement are in fact complementary—for some pathological structures positive MRI contrast media will give clearer images and for others negative contrast media will give the clearer images. Indeed, in certain instances it is advantageous to administer both positive and negative contrast agents to enhance contrast in particular organs or tissues (see Hemmingsen et al. Acta Radiologica 30: 29–33 (1989) Fasc 1).

The contrast enhancing properties of these products also differ in other ways. Thus in general, paramagnetic, positive contrast agents have a relatively close range effect and need to be in close proximity (at the molecular level) to water molecules in order to be effective as contrast agents. Negative contrast agents in the form of magnetically responsive particles have a longer range effect and do not need to be closely adjacent to water molecules or other protons (where the imaging is $^1H$ MRI).

In the GI tract water is absorbed from the contents thus resulting in a reduction in contrast efficiency of paramagnetic substances, especially in the lower part of the alimentary tract. This problem has been addressed by formulation of GdDTPA with an osmoactive agent, that is a compound which enhances water retention in the gut. Thus, for example, EP-A-124766 (Schering AG) and Claussen et al. (supra) report the results of investigations in which patients received an osmoactive oral positive MRI contrast medium containing 1.0 mmol/l GdDTPA and 15 g/l mannitol.

The inclusion of such osmoactive compounds can however cause at least mildly unpleasant side effects for the patients (13 of the 32 patients in the Schering/Claussen et al. study suffered meteorism or diarrhoea), and the inclusion of such compounds in negative contrast media for which the normal absorption of water from the gut contents would not apparently pose a problem would therefore seem to be contraindicated.

We have, however, surprisingly found that formulation of magnetically responsive particles (MRP) with a physiologically tolerable osmoactive agent significantly improves the diagnostic values of the MRP containing MR contrast media.

Thus, in one aspect, the present invention provides a contrast medium comprising magnetically responsive particles and a physiologically tolerable osmoactive agent.

The osmoactive agent in the contrast media of the invention may be any physiologically tolerable osmotically active substance, such as for example: inorganic salts (such as magnesium sulphate); polyols, particularly saccharides or sugar alcohols (see Kirk Othmer "Concise Encyclopedia of Chemical Technology", page 55, John Wiley & Sons, New York) or physiologically tolerable salts thereof or of sugar amino alcohols (especially hexitols such as mannitol or sorbitol); and X-ray contrast agents, especially iodinated water soluble X-ray contrast agents (such as non-ionic and ionic monomers and dimers, e.g. iohexol, diatrizoate meglumine and metrizoate sodium). Such monomers and dimers generally contain one or two triiodophenyl moieties in their molecular structure.

Where X-ray contrast agents are used as osmoactive agents in the MRI contrast media of the invention, there are advantages to both ionic and non-ionic X-ray contrast agents. Thus using ionic X-ray contrast agents, a lower concentration can be used to achieve the same osmotic effect. However, non-ionics are especially suitable for contrast media for administration to young children and persons with perfused or suspected perfusion of the GI system because of the general lower toxicity of non-ionic agents. Another advantage of the non-ionic agents is that they do not precipitate in the stomach.

Examples of suitable non-ionic X-ray contrast agents include, for example, metrizamide (see DE-A-2031724), iopamidol (see BE-A-836355), iohexol (see GB-A-1548594), iotrolan (see EP-A-33426), iodecimol (see EP-A-49745), iodixanol (see EP-A-108638), ioglucol (see U.S. Pat. No. 4,314,055), ioglucomide (see BE-A-846657), iogluniœ (see (DE-A-2456685), iogulamide (see BE-A-882309), iomeprol (EP-A-26281), iopentol (see EP-A-105752), iopromide (see DE-A-2909439), iosarcol (see DE-A-3407473), iosimide (see DE-A-3001292), iotasul (see EP-A-22056), iovarsul (see EP-A-83964) and ioxilan (see WO87/00757).

Where the X-ray contrast agent is ionic, the counter-ion should, of course, be a physiologically tolerable ion, e.g. a metal ion such as sodium, or an organic cation such as meglumine.

Particularly preferred osmoactive agents for the contrast media of the invention include X-ray contrast agents, e.g. iohexol and metrizoate, especially non-ionic X-ray agents and saccharides such as mannitol.

Particular ionic X-ray contrast agents useful according to the invention thus include physiologically acceptable salts of 3-acetylamino-2,4-6-triiodobenzoic acid, 3,5-diacetamido-2,4,6-triiodobenzoic acid, 2,4,6-triiodo-3,5-dipropionamido-benzoic acid, 3-acetylamino-5-((acetylamino)methyl)-2,4,6-triiodobenzoic acid, 3-acetylamino-5-(acetylmethylamino)-2,4,6-triiodobenzoic acid, 5-acetamido-2,4,6-triiodo-N-((methylcarbamoyl)methyl)-isophthalamic acid, 5-(2-methoxyacetamido)-2,4,6-triiodo-N-[2-hydroxy-1-(methylcarbamoyl)-ethyl]-isophthalamic acid, 5-acetamido-2,4,6-triiodo-N-methylisophthalamic acid, 5-acetamido-2,4,6-triiodo-N-(2-hydroxyethyl)-isophthalamic acid 2-[[2,4,6-triiodo-3[(1-oxobutyl)-amino]phenyl]methyl]-butanoic acid, beta-(3-amino-2,4,6-triiodophenyl)-alpha-ethyl-propanoic acid, 3-ethyl-3-hydroxy-2,4,6-triiodophenyl-propanoic acid, 3-[[(dimethylamino)-methyl]amino]-2,4,6-triiodophenyl-propanoic acid (see Chem. Bet. 93: 2347 (1960)), alpha-ethyl-(2,4,6-triiodo-3-(2-oxo-1-pyrrolidinyl)-phenyl)-propanoic acid, 2-[2-[3-(acetylamino)-2,4,6-triiodophenoxy]ethoxymethyl]-butanoic acid, N-(3-amino-2,4,6-triiodobenzoyl)-N-phenyl-β-aminopropanoic acid, 3-acetyl-[(3-amino-2,4,6-triiodophenyl)amino]-2-methylpropanoic acid, 5-[(3-amino-2,4,6-triiodophenyl)methylamino]-5-oxypentanoic acid, 4-[ethyl-[2,4,6-triiodo-3-(methylamino)-phenyl]amino]-4-oxo-butanoic acid, 3,3'-oxybis[2,1-ethanediyloxy-(1-oxo-2,1-ethanediyl)imino]bis-2,4,6-triiodobenzoic acid, 4,7,10,13-tetraoxahexadecane-1,16-dioyl-bis(3-carboxy-2,4,6-triiodoanilide), 5,5'-(azelaoyl-diimino)-bis[2,4,6-triiodo-3-(acetylamino)methyl-benzoic acid], 5,5'-(apidoldiimino)bis(2,4,6-triiodo-N-methyl-isophthalamic acid), 5,5'-(sebacoyl-diimino)-bis(2,4,6-triiodo-N-methylisophthalamic acid), 5,5-[N,N-diacetyl-(4,9-dioxy-2,11-dihydroxy-1,12-dodecanediyl)diimino]bis(2,4,6-triiodo-N-methyl-isophthalamic acid), 5,5'5"-(nitrilo-triacetyltriimino)-tris(2,4,6-triiodo-N-methyl-isophthalamic acid), 4-hydroxy-3,5-diiodo-alpha-phenylbenzenepropanoic acid, 3,5-diiodo-4-oxo-1(4H)-pyridine acetic acid, 1,4-dihydro-3,5-diiodo-1-methyl-4-oxo-2,6-pyridinedicarboxylic acid, 5-iodo-2-oxo-1(2H)-pyridine acetic acid, and N-(2-hydroxyethyl)-2,4,6-triiodo-5-[2,4,6-triiodo-3-(N-methylacetamido)-5-(methylcarbomoyl)benzamino]acetamido]-isophthalamic acid, as well as other ionic X-ray contrast agents proposed in the literature e.g. in J. Am. Pharm. Assoc., Sci Ed. 42:721 (1953), CH-A-480071, JACS 78:3210 (1956), DE-A-2229360, U.S. Pat. No. 3,476,802, Arch. Pharm. (Weinheim, Ger) 306: 11 834 (1973), J. Med. Chem. 6: 24 (1963), FR-M-6777, Pharmazie 16: 389 (1961), U.S. Pat. No. 2,705,726, U.S. Pat. No. 2,895,988, Chem. Ber. 93: 2347 (1960), SA-A-68/01614, Acta Radiol. 12: 882 (1972), GB-A-870321, Rec. Trav. Chim. 87: 308 (1968), East German Patent 67209, DE-A-2050217, DE-A-2405652, Farm Ed. Sci. 28: 912(1973), Farm Ed. Sci. 28: 996 (1973), J. Med. Chem. 9: 964 (1966), Arzheim.-Forsch 14: 451 (1964), SE-A-344166, GB-A-1346796, U.S. Pat. No. 2,551,696, U.S. Pat. No. 1,993,039, Ann 494: 284 (1932), J. Pharm. Soc. (Japan) 50: 727 (1930), and U.S. Pat. No. 4,005,188. The disclosures of these and all other documents cited herein are incorporated herein by reference.

The X-ray contrast agents are more preferred as osmoactive agents than the conventional osmoactive agents such as the mannitol used in the Schering/Claussen et al. studies since the side effects, meteorism and diarrhoea, observed with mannitol should be reduced or eliminated.

The concentration of the osmoactive agent in the contrast media of the invention may vary over a wide range and will be dependent on factors such as the chemical nature of the osmoactive agent, the physical and chemical nature of the MRP (e.g. the size of the magnetic particles) and the other components within the contrast media, the intended administration route, and the pre-administration dilution ratio where the contrast medium is in concentrated form for dilution or dispersion prior to administration.

The appropriate concentration of an osmoactive agent for a contrast medium can readily be selected on the basis of the known properties of the agent or with minimal routine experimentation. Conveniently, however, in a contrast medium ready for administration the osmoactive agent will be present at a concentration of 10 to 800 mmol/l preferably 30 to 400 mmol/l e.g. 2 to 370, especially 5 to 300 mgI/ml for osmoactive agents which are soluble iodinated X-ray contrast agents.

The contrast media of the invention also contains MRPs and there have been many suggestions of suitable MRPs for use as negative contrast agents in MRI. Reference may be had in this regard to the following publications: U.S. Pat. No. 4,863,715 (Jacobsen), WO85/02772 and WO89/03675 (Schröder), U.S. Pat. No. 4,675,173 (Widder), DE-A-3,443,252 (Gries), U.S.

Pat. No. 4,770,183 and WO 88/00060 (Groman), Lönnemark et al. (1989) supra, Laniado et al. (1987) supra, Widder et al. AJR 148: 399–404 (1987), Widder et al. AJR 149: 839 (1988), Mendonca Dias et al. and Olsson et al. Society of Magnetic Resonance in Medicine (SMRM), London 1985, Edelman et al. and Williams et al. Radiology 161(P): 314 (1986), Hahn et al. SMRM, Montreal 1986, Abstracts pages 1537–1538, Hahn et al. Radiology 164: 37 (1987), Hals et al. and Laniado et al. SMRM, Berkeley 1987, Niemi et al. Magnetic Resonance Imaging 6(Suppl. 1): 2 (1988), Hahn et al. Magnetic Resonance Imaging 6(Suppl. 1): 78 (1988) and references therein.

Generally speaking, all such particles may be used in the compositions of the invention. Thus the particles may be free or may be coated by or embedded in or on particles of a non-magnetic carrier material, e.g. a natural or synthetic polymer, for example, cellulose or a sulphonated styrene divinyl-benzene copolymer (see for example WO83/03920 of Ugelstad). The magnetically responsive particles may be ferromagnetic or ferrimagnetic or may be sufficiently small as to be superparamagnetic and indeed superparamagnetic particles are generally preferred.

Thus, the magnetically responsive particles used according to the present invention may be of any material which (although preferably non-radioactive unless the particles are also intended to be detected by their radioactive decay emissions) exhibits ferromagnetism, ferrimagnetism or superparamagnetism. The particles may conveniently be particles of a magnetic metal or alloy, e.g. of pure iron, but particularly preferably will be of a magnetic compound such as a ferrite, for example gamma ferric oxide, magnetite or cobalt, nickel or manganese ferrites.

Particles such as those described by Ugelstad in WO83/03920, by Schröder in WO83/01738, WO85/02772 and WO89/03675, by Molday in U.S. Pat. No. 4,452,773, by Widder in U.S. Pat. No. 4,675,173, by Groman in WO88/00060 and U.S. Pat. No. 4,770,183, by Menz in WO90/01295 and by Lewis in WO90/01899 or those such as Biomag M4200, AMI 26 and M 4125 available from Advanced Magnetics Inc. of Cambridge, Mass., USA, are particularly suitable for use in the compositions of the invention.

To avoid image distortion, it is preferred that the mean particle size of the magnetically responsive particles be less than about 5 micrometers, preferably less than 1 micrometer and that the overall size of the non-magnetic carrier particles be less than 50 micrometers, preferably less than 20 micrometers, especially preferably 0.01 to 5 micrometers, e.g. 0.1 to 5 micrometers. The magnetically responsive particles will generally have mean particle sizes in the range 0.002 to 1 micromaters, preferably 0.005 to 0.2 micrometers.

Where the magnetically responsive particles are carried by carrier particles, these are preferably of a material which is physiologically tolerable and which is not biodegradable, at least in the environments it will experience on the way to and at the body cavity being imaged.

The contrast media of the invention may, of course, include components other than the osmoactive agents and MRPs, for example conventional pharmaceutical or veterinary formulation aids such as wetting agents, disintegrants, binders, fillers, stabilizers, viscosity enhancing agents, flavouring agents, colouring agents, buffers, pH adjusting agents, and liquid carrier media.

The inclusion of buffers in the contrast media of the invention is particularly preferred.

The inclusion of viscosity enhancing agents (e.g. natural, synthetic or semi-synthetic high molecular weight substances, such as gums and polysaccharides, guar gum, tragacanth, methyl cellulose, hydroxypropyl cellulose, carboxymethyl cellulose, xanthan gum, alginates, kaolin, magnesium aluminium silicates and bentonite) in the contrast media of the invention is especially preferred. The viscosity enhancing agent, if present, should be in a concentration sufficient to give the composition the desired viscosity. Desired viscosities can however vary over a broad range depending, for example, on the segment of the GI tract which is to be imaged. Compositions having viscosities of 200 to 5000, especially 300–3000, cps are generally preferred; however, for certain uses compositions having much higher viscosities, e.g. up to 150000 cps or even higher may be used. (Viscosities can conveniently be measured at 20° C. using a Brookfield viscometer).

In one particularly preferred embodiment, the contrast media of the invention are formulated to contain an incompletely hydrated viscosity enhancing agent, e.g. as a dry mix or as a suspension in which the viscosity enhancing agent is provided with a delayed release coating, e.g. of an Eudragit polymer. MRI contrast medium compositions containing incompletely hydrated viscosity enhancing agents are the subject of our copending British Patent Application No. 8916780.3 filed on Jul. 21, 1989.

To improve contact between the MRPs and the walls of the gut (or other body cavity into which the contrast media are administered), the contrast media of the invention may also advantageously contain a mucoadhesive, for example, a polyacrylic acid or a derivative thereof, xanthan gum etc.

The contrast media of the invention may be formulated in a physiologically tolerable aqueous carrier medium (e.g. as a suspension or dispersion) ready for use or in concentrated form for dilution before use. Concentrated products may readily be diluted, e.g. with water or juice, prior to administration. Alternatively, the contrast medium of the invention may be formulated in dry from, e.g. in powder, granule, pellet or tablet from for dispersion before use.

The contrast media of the invention are particularly suited to use, if necessary after dispersion in aqueous media, as MRI contrast media for imaging of the gastrointestinal tract and in particular for imaging the duodenum and the intestines. For such a purpose the contrast medium may be administered orally or rectally or by orally or rectally inserted tubes. However, as indicated above, the contrast media are of course also suitable for use in imaging other externally voided body cavities such as the bladder, uterus and vagina.

Thus, viewed from another aspect, the invention provides the use of a physiologically tolerable osmoactive agent for the manufacture of a contrast medium for use in magnetic resonance imaging.

Viewed from a further aspect, the invention provides the use of magnetically responsive particles for the manufacture of a contrast medium for use in magnetic resonance imaging.

Viewed from a yet further aspect, the present invention provides a method of generating a magnetic resonance image of a human or non-human, e.g. mammalian, subject in which method a contrast medium comprising magnetically responsive particles and an osmoactive agent is administered into an externally voided body cavity of said subject (e.g. the gastrointestinal tract).

Viewed from a yet still further aspect, the invention provides a diagnostic contrast agent kit comprising a plurality of magnetically responsive particles and, packaged separately thereto, a physiologically tolerable osmoactive agent.

In the method of the invention the dose of the contrast medium will generally be at least 30 ml for an adult human subject and more usually 200 to 1500 ml, especially 300 to 1000 ml. In this the magnetically responsive particles will generally be contained at a concentration of 0.01 to 10 g/liter, preferably 0.05 to 3 g/liter, e.g. 0.1 to 3 g/liter. The dose may be taken in portions, e.g. for oral administration about ⅔ being ingested 20 minutes before imaging and the remainder being ingested immediately before the subject is placed in the imager.

The invention is further illustrated by the following non-limiting examples:

EXAMPLE 1

| Suspension for Oral Administration | |
|---|---|
| Magnetic particles* | 10.0 g |
| Hydroxyethyl cellulose | 10.0 g |
| Methyl parahydroxybenzoate | 0.8 g |
| Propyl parahydroxybenzoate | 0.2 g |
| Ethanol | 10.0 g |
| Mannitol | 15.0 g |
| Saccharin sodium | 1.0 g |
| Orange essence | 0.3 g |
| Apricot essence | 0.7 g |
| Water | 952.0 g |

The hydroxyethyl cellulose was dispersed in water with stirring for 2 hours. Saccharin sodium, mannitol and a solution of the essences, and methyl and propyl parahydroxybenzoate in ethanol were slowly added. The magnetic particles were dispersed in the solution under vigorous stirring. The suspension contained 0.05 mg Fe/g.

EXAMPLE 2

| Suspension for Rectal Administration | |
|---|---|
| Methyl parahydroxybenzoate | 85 mg |
| Propyl parahydroxybenzoate | 1 mg |
| Metrizoate sodium | 10 g |
| Methyl cellulose | 2 g |
| Magnetic particles* | 0.5 g |
| Water | 90 ml |

*The magentic particles were Biomag M4200 superparamagnetic particles available from Advanced Magnetics Inc., Cambridge, Massachusetts, U.S.A.

The methyl and propyl parahydroxybenzoates were dissolved in the water at 90° C. After cooling, the metrizoate sodium (prepared according to U.S. Pat. No. 3,476,802) and methyl cellulose were added and the mixture was agitated for 2 hours. The magnetic particles were suspended in the mixture and the suspension was filled into a 100 ml tube. The suspension contained 0.2 mg Fe/ml.

We claim:

1. A contrast medium for enteral use comprising superparamagnetic, ferrimagnetic and ferromagnetic particles and, as a separate chemical entity, a physiologically tolerable osmoactive iodinated X-ray contrast agent, wherein said osmoactive agent is present at a concentration of 10–800 mmol/l.

2. A contrast medium as claimed in claim 1, wherein said particles are coated by or embedded in or on particles of a physiologically tolerable non-magnetic carrier material.

3. A contrast medium as claimed claim 1 containing superparamagnetic particles.

4. A contrast medium as claimed in claim 1 containing particles of material selected from ferrite, gamma ferric oxide, magnetite and cobalt, nickel and manganese ferrites.

5. A contrast medium as claimed in claim 1, wherein said particles have a diameter of less than 5 micrometers.

6. A contrast medium as claimed in claim 1 further containing a physiologically tolerable viscosity enhancing agent.

7. A method of generating a magnetic resonance image of a human or nonhuman mammalian body, said method comprising administering to an externally voided body cavity of said body a contrast medium as claimed in claim 1 and generating a magnetic resonance image of at least part of said body.

8. A contrast medium as claimed in claim 2 containing particles of material selected from ferrite, gamma ferric oxide, magnetite and cobalt, nickel and manganese ferrites.

9. A contrast medium as claimed in claim 3 containing particles of material selected from ferrite, gamma ferric oxide, magnetite and cobalt, nickel and manganese ferrites.

10. A contrast medium as claimed in claim 2 wherein said particles have a diameter of less than 5 micrometers.

11. A contrast medium as claimed in claim 3 wherein said particles have a diameter of less than 5 micrometers.

12. A contrast medium as claimed in claim 4 wherein said particles have a diameter of less than 5 micrometers.

13. A contrast medium as claimed in claim 2 further comprising a physiologically tolerable viscosity enhancing agent.

14. A contrast medium as claimed in claim 3 comprising a physiologically tolerable viscosity enhancing agent.

15. A contrast medium as claimed in claim 4 further comprising a physiologically tolerable viscosity enhancing agent.

16. A contrast medium as claimed in claim 5 further comprising a physiologically tolerable viscosity enhancing agent.

17. A method of generating a magnetic resonance image of a gastrointestinal tract of a human or nonhuman mammalian body, said method comprising administering to the gastrointestinal tract a contrast medium as claimed in claim 1 and generating a magnetic resonance image of the gastrointestinal tract.

18. A method according to claim 17 wherein the iodinated X-ray contrast agent is non-ionic.

19. A diagnostic contrast agent kit comprising a plurality of superparamagnetic, ferrimagnetic or ferromagnetic particles and, packaged separately thereto, a physiologically tolerable osmoactive agent.

* * * * *